United States Patent [19]

Kuo et al.

[11] Patent Number: 5,782,773
[45] Date of Patent: Jul. 21, 1998

[54] THREE-DIMENSIONAL ELECTROCARDIOGRAM DISPLAY METHOD

[75] Inventors: Cheng-Deng Kuo, 8F, No. 314, Sec. 2, Shih-Pi Road, Yun-Shin Li, Pei-Tou, Taipei; Hui-Hua Chiang, Taipei; Chih-Wei Chen, No. 17, Wu-Han Street, Ling-Yai Kao-Shiung, all of Taiwan

[73] Assignees: Chih-Wei Chen; Cheng-Deng Kuo, both of Taipei, Taiwan

[21] Appl. No.: 851,470

[22] Filed: May 5, 1997

[51] Int. Cl.$^6$ ............................................. A61B 5/04
[52] U.S. Cl. ............................................. 600/523
[58] Field of Search ............................ 600/512, 523, 600/525, 544

[56] References Cited

U.S. PATENT DOCUMENTS 4,323,079  4/1982  Demetrescu .................. 600/544
4,478,223  10/1984 Allor ............................... 600/512
4,934,374  6/1990  Ostlund et al. ................. 600/523
5,458,116  10/1995 Egler ............................... 600/512

Primary Examiner—William E. Kamm
Attorney, Agent, or Firm—McDermott, Will & Emery

[57] ABSTRACT

A three-dimensional electrocardiogram display method for 3-D representation of a plurality of cardiac signals is provided. In this method, a 3-D rectangular coordinate system is defined to display the 3-D representation of the cardiac signals. Further, an amplitude display scheme, preferably an amplitude-to-color mapping table, is defined to assign various quantization levels of amplitude to specified distinctive colors. By graphic processing and display means, the 3-D representation of the cardiac signals can be generated and displayed. The physicians can choose to observe the 3-D graph in various views, including perspective view, sectional view, and top rectangular view. This allows the physicians to make diagnosis of heart diseases by observing just one or two 3-D representations of the cardiac signals. The physicians can thus have an overall integral view over a plentiful number of cardiac signals and thereby make diagnosis about the heart conditions of the patient more easily.

19 Claims, 9 Drawing Sheets

THREE-DIMENSIONAL ELECTROCARDIOGRAM DISPLAY METHOD

BACKGROUND OF THE INVENTION

1. Field of the Invention

This invention relates in general to electrocardiogram (abbreviated as ECG or EKG) display methods, and more particularly, to a three-dimensional (3-D) EKG display method for a set of cardiac signals.

2. Description of Related Art

An electrocardiograph is a medical tool devised to measure and record the electrical activities of the heart of a patient. In order to record an ECG waveform, a differential recording between two points (i.e., the potential difference between the two points) on the body are made. Traditionally, each differential recording is referred to as a lead which represents one single cardiac signal from the body. The waveform patterns of the cardiac signals can be visually displayed by graphic display means. Each cardiac signal shows particular waveform that may indicate signs of certain heart diseases. By visually inspecting the waveforms of the cardiac signals, physicians can make diagnoses about the heart conditions of the patient to thereby determine if the patient suffers from certain heart disorders such as myocardinal infarction, conduction defects, atrial and ventricular hypertrophy, and so on.

The records of the cardiac electrical activities are referred to as electrocardiograms. The electric activity of the heart can be detected and recorded by attaching a number of electrodes to the body's surface. The so-called standard 12-lead EKG is presently the most widely used EKG recording technology in clinical applications.

The standard 12-lead EKG includes a first set of six horizontal-plane cardiac signals, which are customarily designated by $[V_1, V_2, V_3, V_4, V_5, V_6]$, and a second set of six frontal-plane cardiac signals, which are customarily designated by $[I, II, III, \alpha V_L, \alpha V_R, \alpha V_F]$. The two-dimensional amplitude-versus-time characteristic plots of these twelve cardiac signals form twelve graphs which are collectively referred to as the standard 12-lead EKG. The measurements of these twelve cardiac signals are briefly described in the following.

(A) Horizontal-Plane Cardiac Signals

The horizontal-plane cardiac signals $[V_1, V_2, V_3, V_4, V_5, V_6]$ are electrical signals originated from the activities of the heart of a patient, which are measured through a set of six unipolar electrode leads attached on particular positions along a curve (hereinafter referred to as precordial curve) on the patient's chest. The horizontal-plane cardiac signals $[V_1, V_2, V_3, V_4, V_5, V_6]$ are obtained by the following manner:

$$V_i = V_{pi} - V_W \quad (A\text{-}1)$$

for i=1 to 6
where $[V_{p1}, V_{p2}, V_{p3}, V_{p4}, V_{p5}, V_{p6}]$ are the potentials measured at the six unipolar precordial leads; and $V_W$ is the potential measured at a common node which ties the left-arm lead, the right-arm lead, and the left-leg lead together.

(B) Frontal-Plane Cardiac Signals

Among the six frontal-plane cardiac signals $[I, II, III, \alpha V_L, \alpha V_R, \alpha V_F]$, the first three cardiac signals $[I, II, III]$ are obtained through three bipolar standard leads, and the other three cardiac signals $[\alpha V_L, \alpha V_R, \alpha V_F]$ are obtained through three unipolar augmented extremity leads.

The cardiac signals $[I, II, III]$ are obtained by the following equations:

$$I = V_{LA} - V_{RA} \quad (B\text{-}1)$$

$$II = V_{LL} - V_{RA} \quad (B\text{-}2)$$

$$III = V_{LL} - V_{LA} \quad (B\text{-}3)$$

where $V_{LA}$ is the potential measured at the left-arm lead (LA= left arm);

$V_{RA}$ is the potential measured at the right-arm lead (RA=right arm); and $V_{LL}$ is the potential measured at the left-leg lead (LL=left leg);

and the cardiac signals $[\alpha V_L, \alpha V_R, \alpha V_F]$ are obtained by the following equations:

$$aVL = \frac{2 \cdot V_{LA} - V_{RA} - V_{LL}}{2} \quad (B\text{-}4)$$

$$aVR = \frac{2 \cdot V_{RA} - V_{LA} - V_{LL}}{2} \quad (B\text{-}5)$$

$$aVF = \frac{2 \cdot V_{LL} - V_{LA} - V_{RA}}{2} \quad (B\text{-}6)$$

The two-dimensional amplitude-versus-time characteristic plots of the foregoing twelve cardiac signals $[V_1, V_2, V_3, V_4, V_5, V_6]$ and $[I, II, III, \alpha V_L, \alpha V_R, \alpha V_F]$ are collectively referred to as the standard 12-lead EKG. Fundamentally, the amplitude-versus-time characteristic plot of each cardiac signal includes a P-wave portion, a QRS-complex wave portion, and a T-wave portion. Physicians can observe these particular wave portions to see if there are any abnormalities, and thereby make diagnoses about the heart condition of the patient.

All of the above-mentioned cardiac signals and their measurement methods are conventional techniques which are well-known to those skilled in the field of electrocardiograms, so that description thereof will not be further detailed. For details, novice readers can refer to suitable textbooks on the principles of electrocardiography.

Conventionally, these twelve cardiac signals $[V_1, V_2, V_3, V_4, V_5, V_6]$ and $[I, II, III, \alpha V_L, \alpha V_R, \alpha V_F]$ are displayed by means of multi-channel monitors and recorders in 2-D graphs which can also be plotted on paper by graphic output devices, such as plotters or printers, so that they can be visually inspected by the physicians. These 2-D graphs are the traces of the amplitude-versus-time characteristic of the cardiac signals. To make a diagnosis about the heart conditions of an individual patient, the physician has to visually inspect twelve 2-D graphs (i.e., the standard 12-lead EKG) for any abnormal feature in the P-wave, QRS-complex wave, and T-wave portions of the waveform which are indicative of certain heart diseases. Since twelve graphs are quite a plentiful amount of data, the diagnosis procedure is quite laborious and time-consuming. It is also difficult for newcomers to learn and master the skill quickly.

SUMMARY OF THE INVENTION

It is therefore a primary objective of the present invention to provide a 3-D EKG display method which can integrate the cardiac information from a set of cardiac signals in a single 3-D graph for the physician to make diagnoses more easily.

In accordance with the foregoing and other objectives of the present invention, a novel 3-D EKG display method is provided.

In this 3-D EKG display method, a 3-D rectangular coordinate system is defined, which has a temporal axis representing the time domain of the cardiac signals, a spatial axis representing the positions where the cardiac signals are extracted, and an amplitude axis representing the amplitudes of the cardiac signals. Further, an amplitude display manner is defined, which assigns the various quantization levels of the amplitudes of the cardiac signals to predetermined display manners, preferably distinctive colors.

A 3-D representation of the cardiac signal can then be displayed based on the 3-D rectangular coordinate system and the amplitude display manner. The physicians can choose to display the 3-D graph in various views, including perspective view, sectional view, and top rectangular view.

In the first preferred embodiment of the method of the invention, the cardiac signals are the six horizontal-plane cardiac signals [$V_1$, $V_2$, $V_3$, $V_4$, $V_5$, $V_6$] extracted from the precordial curve on the patient's chest. In the second preferred embodiment, the cardiac signals are the six frontal-plane cardiac signals [I, II, III, $\alpha V_L$, $\alpha V_R$, $\alpha V_F$]. This allows the 12 cardiac signals of the standard 12-lead EKG to be displayed only in two 3-D graphs instead of 12 2-D graphs as by the conventional EKG method.

The invention allows the physicians to observe the features indicative of specific heart diseases in each of the six cardiac signals [$V_1$, $V_2$, $V_3$, $V_4$, $V_5$, $V_6$] collectively in one single 3-D graph, and the same in each of the six cardiac signals [I, II, III, $\alpha V_L$, $\alpha V_R$, $\alpha V_F$] collectively in another 3-D graph. By viewing the 3-D graphs, the physicians can have an overall integral view over the plentiful number of cardiac signals from the patient, thus allowing the physicians to make diagnoses more easily.

BRIEF DESCRIPTION OF DRAWINGS

The invention can be more fully understood from the following detailed description of the preferred embodiments, with reference made to the accompanying drawings, wherein.

DETAILED DESCRIPTION OF PREFERRED EMBODIMENT

In the following detailed disclosure of the invention, two preferred embodiments will be disclosed. The first preferred embodiment is used to display the six horizontal-plane cardiac signals [$V_1$, $V_2$, $V_3$, $V_4$, $V_5$, $V_6$] in one single 3-D graph; and the second preferred embodiment is used to display the six frontal-plane cardiac signals [I, II, III, $\alpha V_L$, $\alpha V_R$, $\alpha V_F$] in another 3-D graph.

First Preferred Embodiment (The Precordial 3-D Embodiment)

Figure 1:
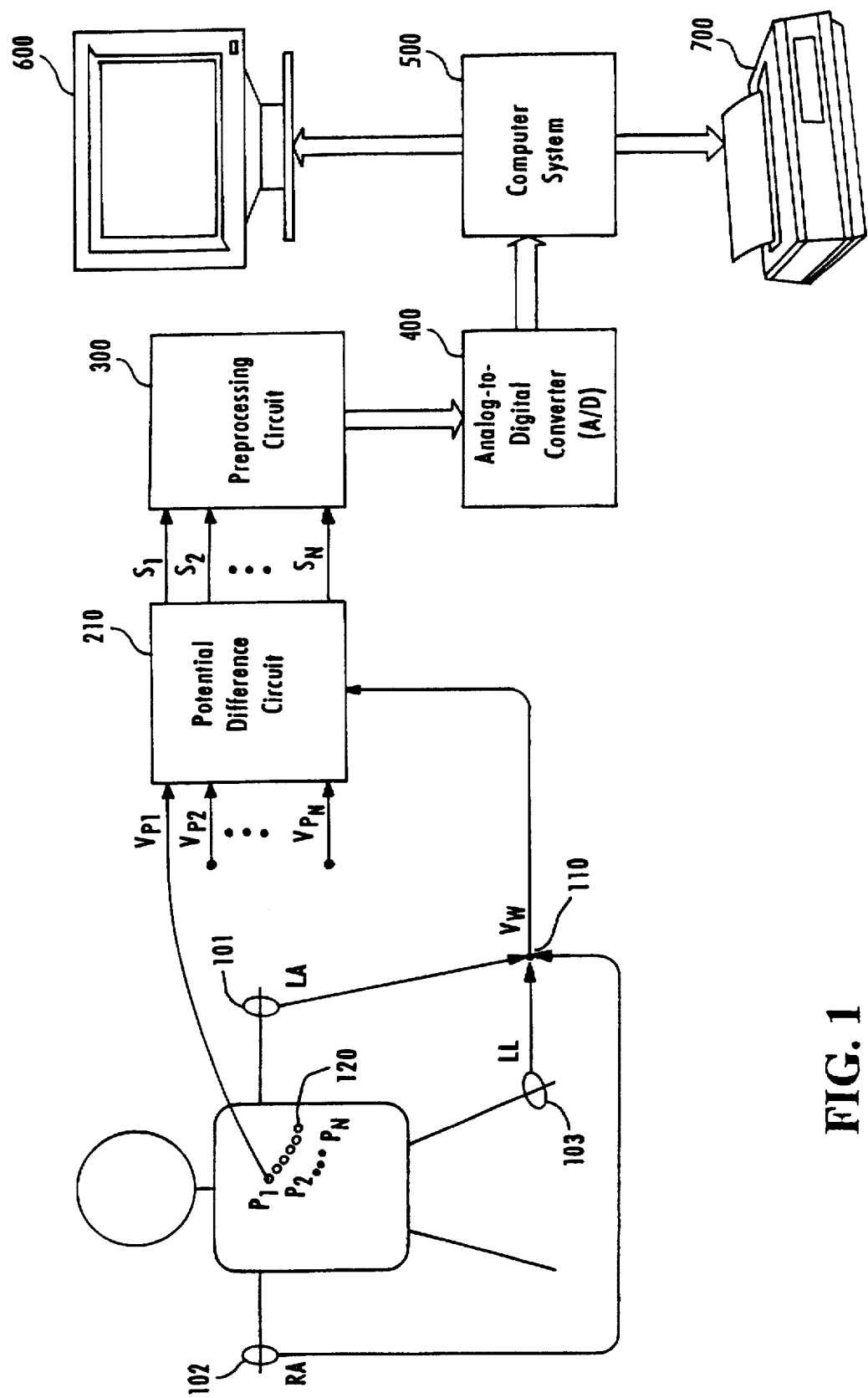
FIG. 1 is a schematic diagram of an EKG system configured in accordance with the 3-D EKG display method of the invention.

Referring to FIG. 1, here is shown a schematic diagram of an EKG system configured in accordance with the first preferred embodiment of the 3-D EKG display method of the invention (referred to as the precordial 3-D embodiment). To use this EKG system to check the heart conditions of a patient, a left-arm electrode 101 is attached to his/her left-hand wrist, a right-arm electrode 102 is attached to his/her right-hand wrist, and a left-leg electrode 103 is attached to his/her left-leg foot. Further, these three electrodes 101, 102, 103 are wired to a common node 110. Assume that the potential measured at the common node 110 is $V_W$, which is basically always zero in magnitude.

Figure 2:
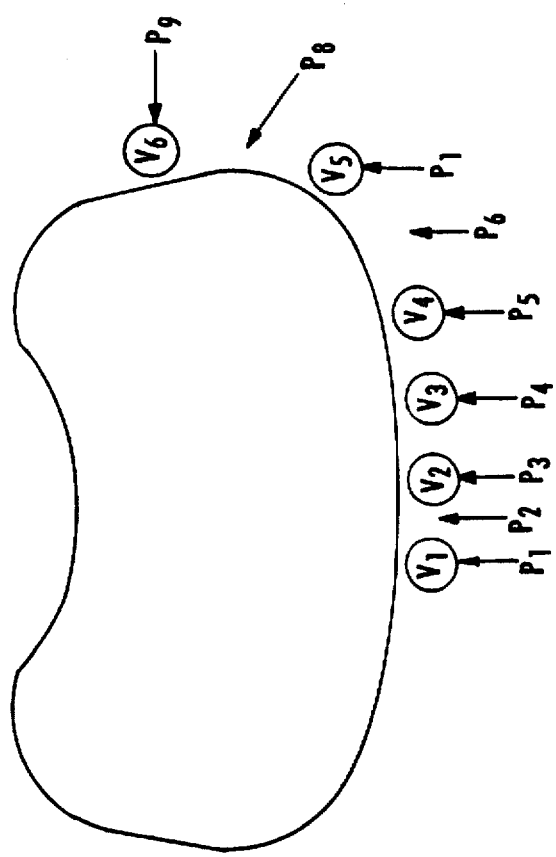
FIG. 2 is a schematic diagram showing the placement of 9 electrodes on the precordial curve on a patient's chest.

Further, a number of N electrodes 120 are attached to the precordial curve on the patient's chest where the horizontal-plane cardiac signals [$V_1$, $V_2$, $V_3$, $V_4$, $V_5$, $V_6$] are customarily extracted. The positions on which the N electrodes are attached are respectively designed by $P_1$, $P_2$, . . . , and $P_N$. The number of these electrodes can be any integer number greater than 1, but $N \geq 6$ is preferable for more precise 3-D construction of the six horizontal-plane cardiac signals [$V_1$, $V_2$, $V_3$, $V_4$, $V_5$, $V_6$]. If N=6, the six electrodes are attached exactly to the positions where the six horizontal-plane cardiac signals [$V_1$, $V_2$, $V_3$, $V_4$, $V_5$, $V_6$] are customarily extracted. If N>6, the N electrodes are attached at suitable intervals along the precordial curve on the patient's chest. Taking N=9 as example, the nine electrodes can be attached in a manner as illustrated in FIG. 2 and depicted as follows.

$P_1 \rightarrow$ the position of $V_1$
$P_2 \rightarrow$ the mid-point position between $V_1$ and $V_2$
$P_3 \rightarrow$ the position of $V_2$
$P_4 \rightarrow$ the position of $V_3$
$P_5 \rightarrow$ the position of $V_4$
$P_6 \rightarrow$ the mid-point position between $V_4$ and $V_5$
$P_7 \rightarrow$ the position of $V_5$
$P_8 \rightarrow$ the mid-point position between $V_5$ and $V_6$
$P_9 \rightarrow$ the position of $V_6$ The foregoing arrangement allows the horizontal-plane cardiac signals [$V_1$, $V_2$, $V_3$, $V_4$, $V_5$, $V_6$] to be evenly extracted by the nine electrodes.

There is no upper limit to the number N. The greater the number N, the higher will be the resolution of the resultant 3-D graph. However, a greater N needs an increased number of electrodes which should be made smaller in size so that the length of the precordial curve can accommodate this large number of electrodes thereon. Further, a more complex hardware circuit should be devised to handle the large number of cardiac signals from these large number of electrodes. The cost will thus be increased with the number N of the electrodes. The designer can choose a suitable N which represents a tradeoff between the resolution and the cost.

Referring back to FIG. 1, the EKG system includes a potential difference circuit 210, a preprocessing circuit 300, an analog-to-digital (A/D) converter 400, a computer system 500, a color monitor 600, and a color printer 700 for signal processing and 3-D representation of the cardiac signals. Assume that the potentials measured at the N electrodes 120 on the N positions $[P_1, P_2, \ldots, P_N]$ on the precordial curve on the patient's chest are $[V_{P1}, V_{P2}, \ldots, V_{PN}]$. These potentials $[V_{P1}, V_{P2}, \ldots, V_{PN}]$, along with the potential $V_W$ at the common node 110, are connected to a potential difference circuit 210. This potential difference circuit 210 is configured in such a manner as to obtain the potential difference between each of the potentials $[V_{P1}, V_{P2}, \ldots, V_{PN}]$ and the common-node potential $V_W$ to thereby output a set of voltage signals $[S_1, S_2, \ldots, S_N]$ by the following equation:

$$S_i = V_{Pi} - V_W$$

for i=1 to N

These N voltage signals $[S_1, S_2, \ldots, S_N]$, which are in analog form represent N horizontal-plane cardiac signals from the precordial curve on the patient's chest. These cardiac signal $[S_1, S_2, \ldots, S_N]$ may be small in amplitude and contain noises or undesired signal components, such as the phenomenon of signal drifting caused by the breathing action of the patient. Therefore, they are first processed by the preprocessing circuit 300, which includes analog amplification means and various filtering means (not shown), so as to amplify the N cardiac signals $[S_1, S_2, \ldots, S_N]$ to suitable levels for subsequent processing and to filter out the noises and undesired components. The detailed circuit design for these analog amplification and filtering means involves basic circuit design techniques that are apparent to those skilled in the art when the specifications are present, so that description thereof will not be further detailed. Alternatively, the preprocessing circuit 300 can also be implemented by a digital signal processor (DSP) which is coupled in subsequent cascade to the A/D converter 400 so as to perform the filtering by digital filters.

The output of the preprocessing circuit 300 is subsequently processed by the A/D converter 400 so as to convert each of the N cardiac signals $[S_1, S_2, \ldots, S_N]$ into digital form. In this A/D converter 400, the amplitude is divided into a number of quantization levels. Each cardiac signal is sampled at a predetermined period and then digitally converted in accordance with the quantization level of the amplitude. Detailed circuit structure and functions of the A/D converter 400 are well-known in the art so that description thereof will not be further detailed.

The digitized cardiac signals $[S_1, S_2, \ldots, S_N]$ are then fed to the computer system 500. This computer system 500 can be a personal computer or a high-end workstation with high-performance graphics capabilities. The color monitor 600 connected to the computer system 500 is used to visually display the 3-D representation of the cardiac signals $[S_1, S_2, \ldots, S_N]$ in accordance with the method of the invention, and the color printer 700 can be used to print the same 3-D cardiac signals on paper.

The computer system 500 runs a graphic software program having a 3-D graphic capability. In this embodiment, the MATLAB program is used to process the digitized cardiac signals and generate a 3-D representation of the cardiac signals in accordance with the method of the invention. However, other software programs having similar graphic capabilities can be used.

Figure 3:
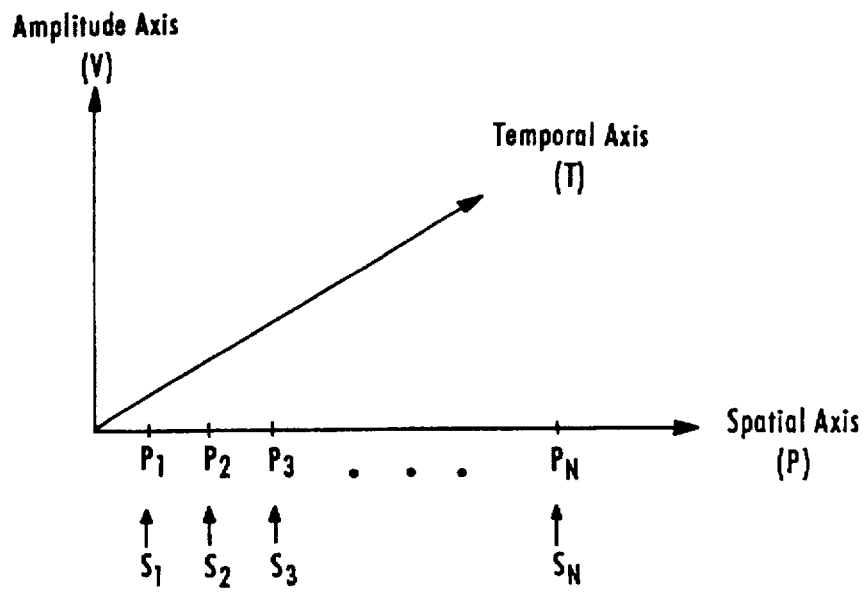
FIG. 3 is a schematic diagram of a 3-D rectangular coordinate system used to display a 3-D graph in accordance with the invention.

To allow the MATLAB program to generate a 3-D representation of the cardiac signals $[S_1, S_2, \ldots, S_N]$, a 3-D rectangular coordinate system as shown in FIG. 3 and an amplitude display table are predefined and built into the program.

Referring to FIG. 3, the 3-D rectangular coordinate system is defined in such a manner that the three axes thereof are respectively named spatial axis (P), temporal axis (T), and amplitude axis (V). The spatial axis (P) represents the spatial positions $[P_1, P_2, \ldots, P_N]$ on the precordial curve on the patient's chest where the cardiac signals $[S_1, S_2, \ldots, S_N]$ were extracted; the temporal axis (T) represents the time domain of these cardiac signals $[S_1, S_2, \ldots, S_N]$; and the amplitude axis (V) represents the amplitude of each of these cardiac signal $[S_1, S_2, \ldots, S_N]$.

On the spatial axis (P), the spatial positions $[P_1, P_2, \ldots, P_N]$ are preferably arranged in the order shown, since the phase angles of these cardiac signal $[S_1, S_2, \ldots, S_N]$ are also ordered in such a manner. This allows two neighboring cardiac signals to have the smallest difference in phase angle such that the resultant 3-D graph will have smooth gradations from one cardiac signal to the next.

When N is small, for example when N=9, the interval between two neighboring cardiac signals on the spatial axis (P) will be large. This will cause the resultant 3-D graph to display abrupt gradations between two neighboring cardiac signals which are usually considered poor visual quality. In order to make the surfaces of the 3-D graph smooth, one additional spatial point can be placed at the middle of each pair of neighboring cardiac signals, and the amplitude values of these points are obtained by interpolation. In the case of N=9, an additional 8 points can be built such that the spatial axis (P) includes 17 spatial points of the cardiac signals. The amplitude values of these additional points are determined by interpolation. This allows the resultant 3-D graph to display smooth surfaces.

However, if N=17 (i.e., 17 electrodes are attached on the precordial curve on the patient's chest), this interpolation process can be omitted.

Figure 4:
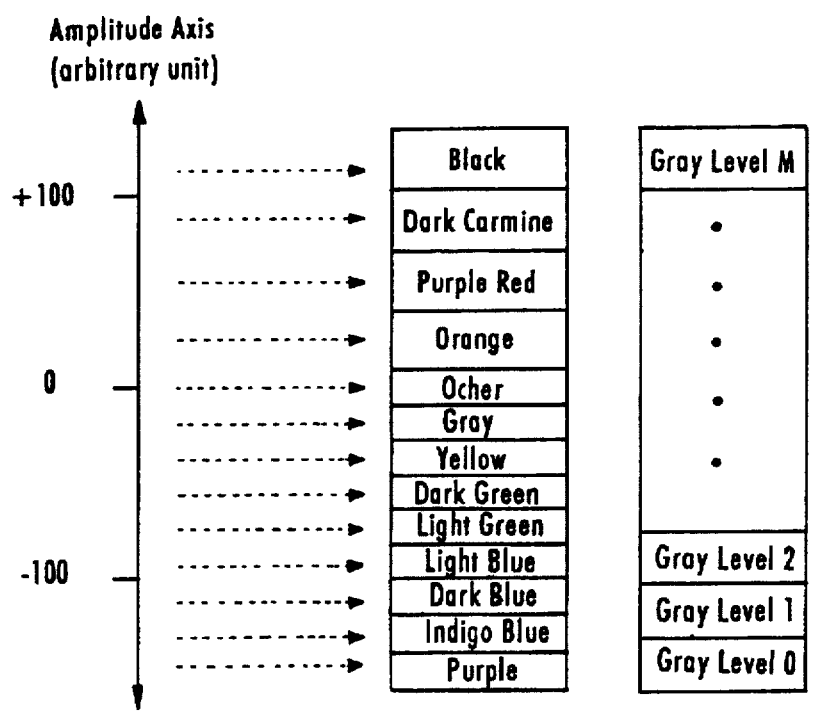
FIG. 4 is a schematic diagram used to show the mapping of quantization levels of cardiac signal amplitude to either a color table or a grayscale.

Referring further to FIG. 4, after the 3-D rectangular coordinate system is defined, the next step is to define an amplitude display table which determines how each quantization level of the amplitude is to be visually displayed. In the embodiments disclosed here, the amplitude display table can be either an amplitude-to-color mapping table or an amplitude-to-grayscale mapping table as shown in FIG. 4.

According to the amplitude-to-color mapping table, the quantization levels of the amplitude are mapped from the lowest level to the highest level respectively to one of a selected set of distinctive colors, including purple, indigo blue, dark blue, light blue, light green, dark green, yellow, gray, ocher, orange, purple red, dark carmine, and black, for example. This allows the resultant 3-D graph to be displayed with distinctive color representations for different levels of the amplitude. The amplitude-to-color mapping table shown here represents a design scheme by the inventor and is not intended to limit the scope of the invention. The assignment of colors in the amplitude-to-color mapping table can be arbitrary or specified so as to show the best visual effect for the resultant 3-D graph.

By using the amplitude-to-grayscale mapping table, for example, the quantization levels of the amplitude are mapped in a one-on-one manner to one gray level in the grayscale. The number of gray levels in the grayscale is dependent on the number of the quantization levels of the amplitude. Alternatively, the grayscale can be replaced by a colorscale of a selected color.

Still more, the different quantization levels of the amplitude can be displayed in contour lines when the 3-D graph is displayed in top rectangular view. Nevertheless, the scheme of using the amplitude-to-color mapping table is considered by the inventor as the best mode embodiment of the invention since the color representation allows the human eye to easily distinguish the minute variations in the 3-D graph.

Based on the 3-D rectangular coordinate system and the amplitude display table defined in the foregoing, the MATLAB program can generate a 3-D representation of the input cardiac signals $[S_1, S_2, \ldots, S_N]$.

Figure 5:
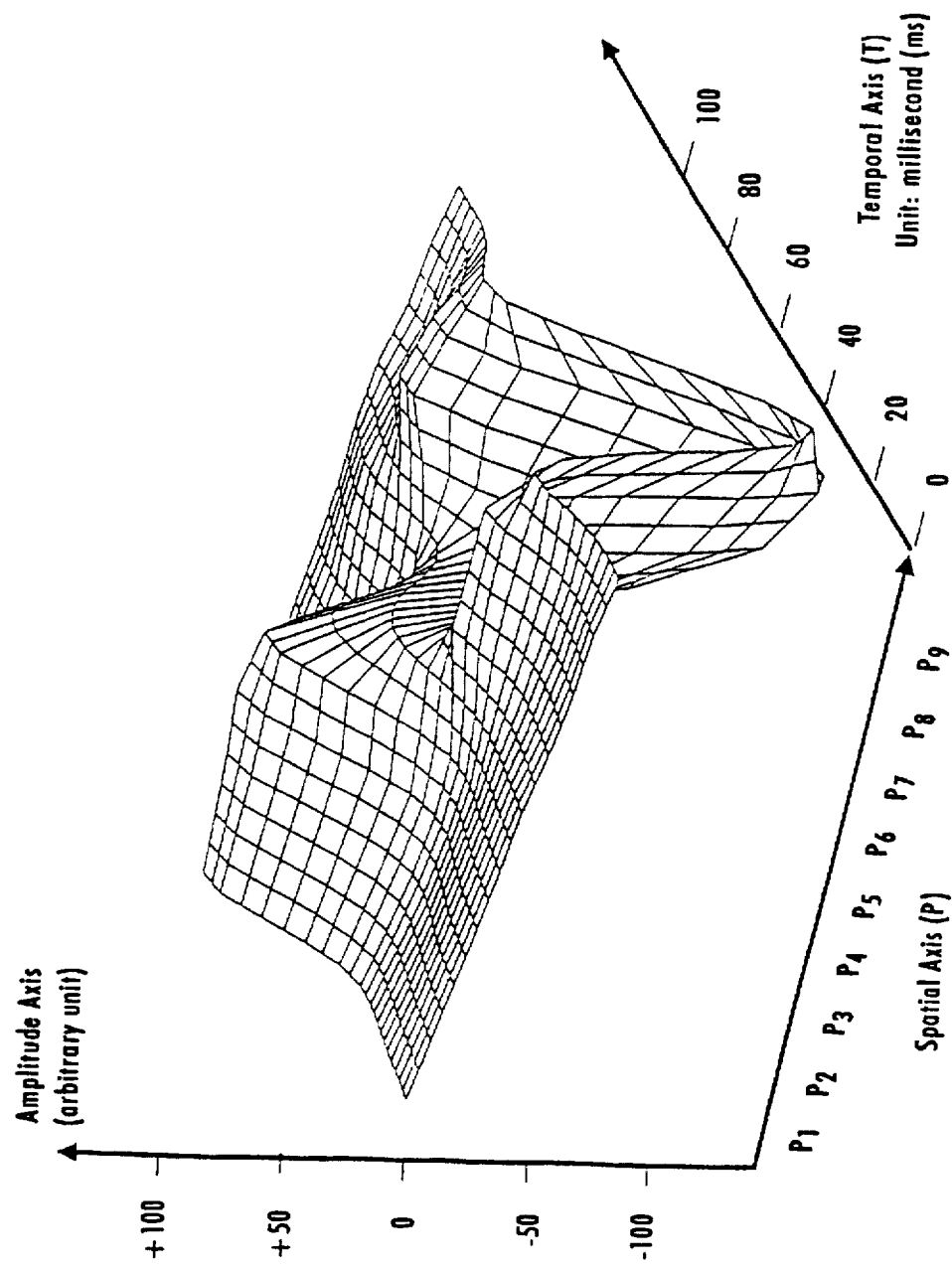
FIG. 5 shows a demonstrative 3-D graph obtained by the 3-D EKG display method of the invention.

One example of the 3-D graph is illustrated in perspective view in FIG. 5. This graph is only illustrated for demonstrative purpose, in which only a 0.1 sec. duration of the cardiac information including solely the QRS-complex wave is displayed.

Further, the 3-D graph can be displayed in either a static or a dynamic manner. In static display manner, the displayed 3-D graph is a still picture which represents the cardiac signals extracted during a selected fixed period of the heartbeat. In dynamic display manner, the displayed 3-D graph is refreshed with each heartbeat of the patient.

The 3-D graph can be displayed in various views based on user-selection, including perspective view, sectional view, and top rectangular view. In perspective view, the physicians can rotate the 3-D graph in all directions so as to view the 3-D graph in various aspects. In sectional view, the physicians can choose to view either a V-T plane or a P-T plane sectional view of the 3-D graph.

The V-T plane sectional view crossing a particular spatial point, say $P_j$, on the spatial axis (P), represents a 2-D representation of the cardiac signal extracted from that point $P_j$. This allows the physicians to view the amplitude-time characteristic of a particular cardiac signal in the same way as the conventional EKG method which displays the standard 12-lead EKG.

The P-T plane sectional view crossing a particular temporal point (time) on the temporal axis (T) shows the amplitude distribution of all of the cardiac signals $[S_1, S_2, \ldots, S_N]$ over the precordial curve on the patient's chest. This sectional view is useful for the physicians to view the amplitude distribution of all of the cardiac signals $[S_1, S_2, \ldots, S_N]$ in a collective manner.

The sectional view can also be displayed in either a static or a dynamic manner. In static display manner, the displayed sectional view is a still picture which shows the amplitude-time characteristic (for V-T plane sectional view) or amplitude distribution (for P-T plane sectional view) during a selected fixed period of the heartbeat. In dynamic display manner, the displayed sectional view is refreshed with each heartbeat of the patient.

Figure 6A:
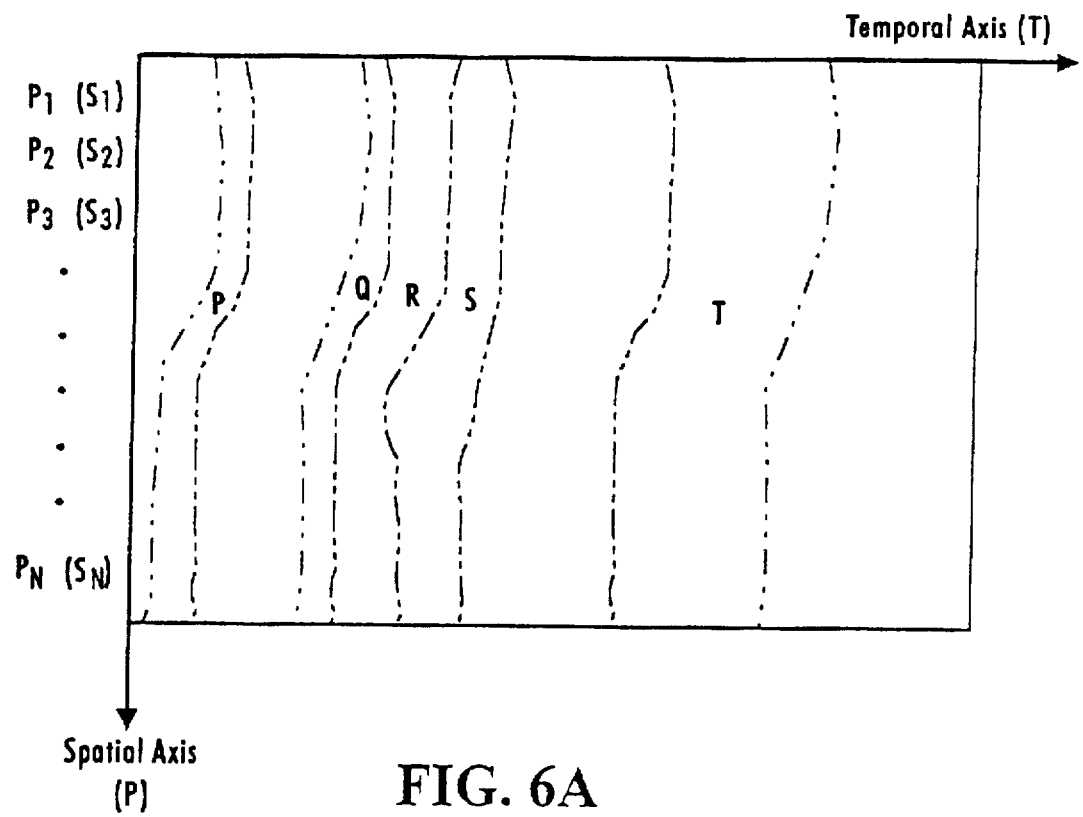
FIG. 6A is a schematic diagram of the top rectangular view of the 3-D representation of the horizontal-plane cardiac signals.

Further, the 3-D graph can be displayed in a top rectangular view, as schematically illustrated in FIG. 6A. For each heartbeat of the patient, the top rectangular view shows a P-wave region, a QRS-complex wave region, and a T-wave region. These regions are displayed with distinctive colors or gray levels in accordance with the predefined amplitude display manner described above. In the case of the amplitude-to-color mapping table (which is the best mode embodiment of the method of the invention), these regions can be easily distinguished visually from each other by physicians since they are displayed in distinctive colors corresponding to their different amplitude ranges. Therefore, if the patient has a heart disease, the corresponding variations in the P-wave, QRS-complex wave, and T-wave in each of the cardiac signals $[S_1, S_2, \ldots, S_N]$ can here be collectively observed by the physicians by viewing one single 3-D graph instead of six 2-D graphs obtained by the conventional EKG method.

Figure 6B:
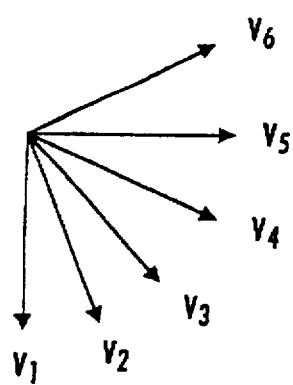
FIG. 6B is a schematic diagram of the top sectoral view of the 3-D graph, showing the phase relationship among the horizontal-plane cardiac signals displayed in the 3-D graph.

Further, the physicians can also choose to display a top sectoral view as illustrated in FIG. 6B to see the phase relationship among the displayed cardiac signals.

Second Preferred Embodiment (The Limb-lead 3-D Embodiment)

Figure 7:
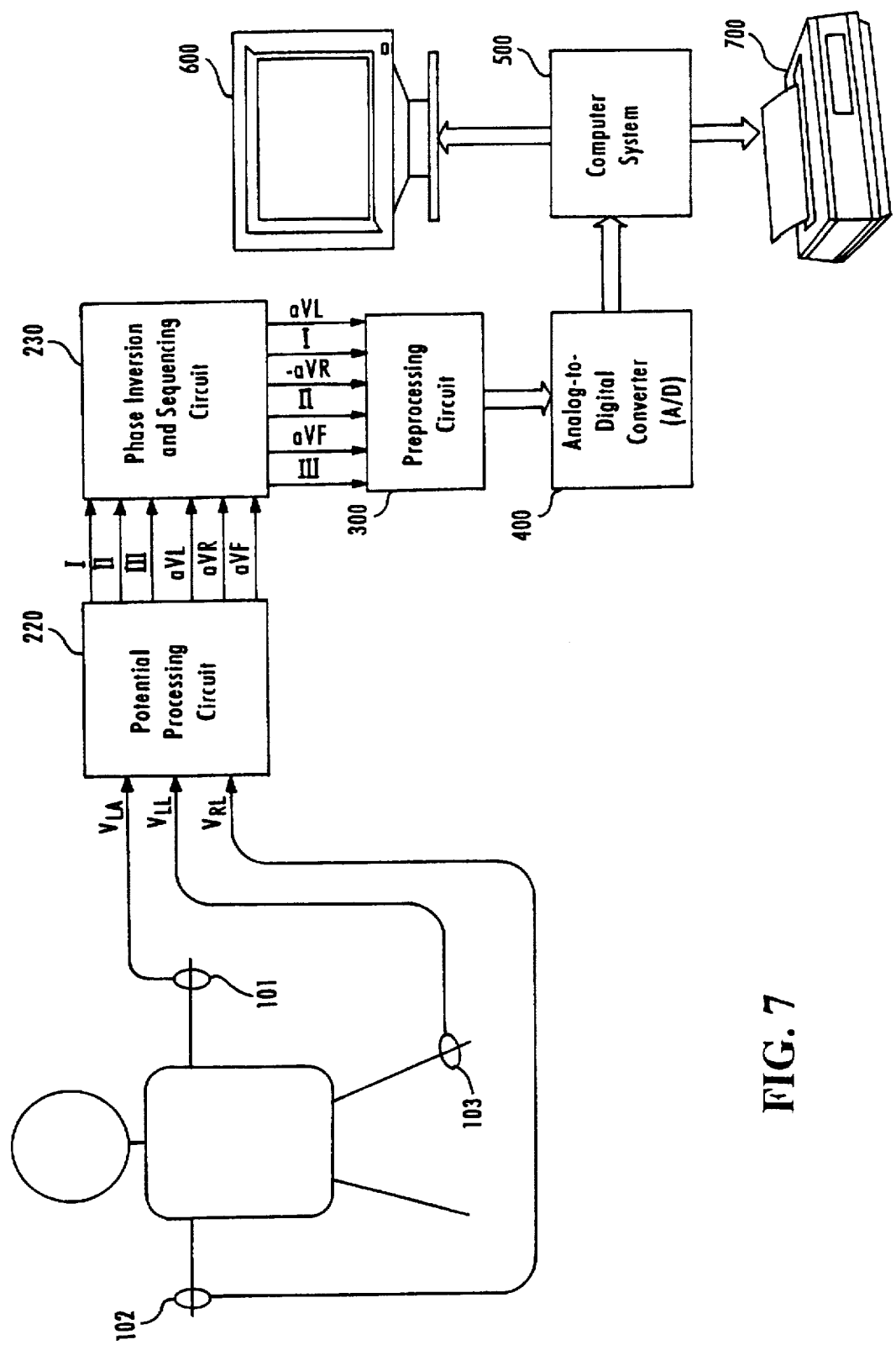
FIG. 7 is a schematic diagram of another EKG system configured in accordance with the 3-D EKG display method of the invention.

Referring to FIG. 7, here is shown a schematic diagram of an EKG system configured in accordance with the second preferred embodiment of the 3-D EKG display method of the invention (referred to as the limb-lead 3-D embodiment). This EKG system is devised in particular to display a 3-D representation of the six frontal-plane cardiac signals [I, II, III, $\alpha V_L$, $\alpha V_R$, $\alpha V_F$].

In this EKG system, the left-arm electrode 101 is used to take the measurement of the left-arm potential $V_{LA}$; the right-arm electrode 102 is used to take the measurement of the left-leg potential $V_{LL}$; and the left-leg electrode 103 is used to take the measurement of the right-leg potential $V_{RL}$ from the patient. These three potentials $[V_{LA}, V_{LL}, V_{RL}]$ are fed to a potential processing circuit 220 which then outputs the six frontal-plane cardiac signals [I, II, III, $\alpha V_L$, $\alpha V_R$, $\alpha V_F$] in accordance with Eqs. (B-1) through (B-6) as given in the background section of this specification. Since the conversion from $[V_{LA}, V_{LL}, V_{RL}]$ to [I, II, III, $\alpha V_L$, $\alpha V_R$, $\alpha V_F$] are the same as the conventional EKG method, the circuit structure of the potential processing circuit 220 will not be further detailed.

Figure 8A:
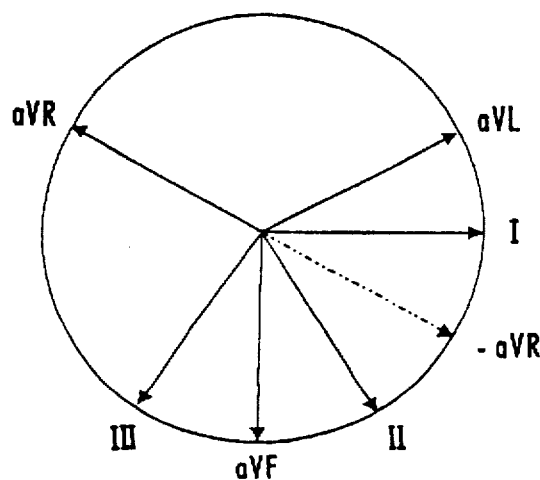
FIGS. 8A and 8B are schematic diagrams showing the phase relationship among the frontal-plane cardiac signals on the phase plane.
Figure 8B:
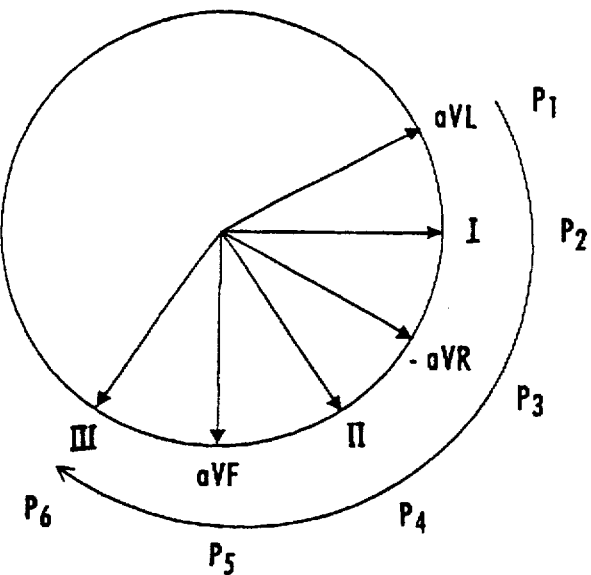

As described earlier in this section, the resultant 3-D graph will have smooth surfaces and gradations from one cardiac signal to the next if the cardiac signals are arranged on the spatial axis (P) according to the order of their phase angles. The phase relationship of these cardiac signals [I, II, III, $\alpha V_L$, $\alpha V_R$, $\alpha V_F$] is illustrated schematically in FIG. 8A. It can be seen that the phase angle of the cardiac signal $\alpha V_R$ is particularly far away from the other cardiac signals. To allow for smooth surfaces and gradations in the resultant 3-D graph, the cardiac signal $\alpha V_R$ can be inverted in phase angle to obtain -$\alpha V_R$ as illustrated in FIG. 8B. After this, the resultant new set of cardiac signals [$\alpha V_L$, I, -$\alpha V_R$, II, $\alpha V_F$, III] are substantially spaced at equal intervals on the phase plane. Starting clockwise from $\alpha V_L$, these cardiac signals [$\alpha V_L$, I, -$\alpha V_R$, II, $\alpha V_F$, III] are then arranged on the spatial axis (P) according to the order of their phase angles, as illustrated in FIG. 9.

The phase inversion is not limited to the foregoing manner. Alternatively, for example, the two cardiac signals $\alpha V_L$ and I can be inverted in phase angle to obtain the sequence [II, $\alpha V_F$, III, -$\alpha V_L$, -I, $\alpha V_R$], or the three cardiac signals II, $\alpha V_F$, and III can be inverted in phase angle to obtain the sequence [$\alpha V_R$, -II, -$\alpha V_F$, -III, $\alpha V_L$, I]. However, since two or more cardiac signals are to be inverted in phase angle, the hardware for implementing the phase inversion process will be more complex and costly than the previous scheme in which only the cardiac signal $\alpha V_R$ is inverted in phase angle. Therefore, for the best mode embodiment of the invention, the sequence [$\alpha V_L$, I, -$\alpha V_R$, II, $\alpha V_F$, III] is used.

Figure 9:
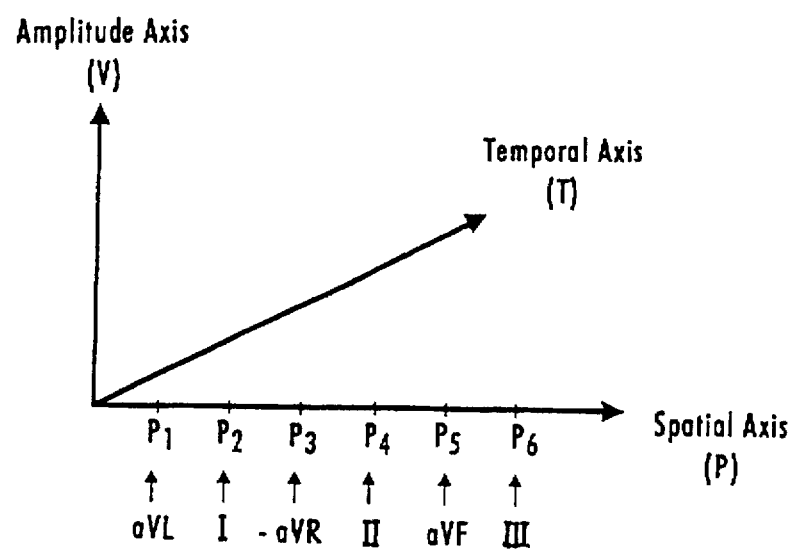
FIG. 9 is a schematic diagram of a 3-D rectangular coordinate system used to display a 3-D graph in accordance with the invention.

Referring back to FIG. 7, the output cardiac signals [I, II, III, $\alpha V_L$, $\alpha V_R$, $\alpha V_F$] from the potential processing circuit 220 are fed in parallel to a phase-inversion and sequencing circuit 230 which is devised in such a way as to invert the phase angle of at least one of cardiac signals, in this case $\alpha V_R$, and then output the cardiac signals in the following order: [$\alpha V_L$, I, -$\alpha V_R$, II, $\alpha V_F$, III], so as to arrange them in the order shown on the spatial axis (P), as illustrated in FIG. 9. The detailed circuit structure of the phase-inversion and sequencing circuit 230 is apparent to those skilled in the art when the foregoing functions are presented, so that it will not be further detailed. The output cardiac signals [$\alpha V_L$, I, $-\alpha V_R$, II, $\alpha V_F$, III] from the phase-inversion and sequencing circuit 230 are fed to the preprocessing circuit 300. This preprocessing circuit 300 and the subsequent A/D converter 400, computer system 500, color monitor 600, and color printer 700 are all the same in functionality as those shown and described with reference to FIG. 1, so that description thereof will not be repeated.

Figure 10A:
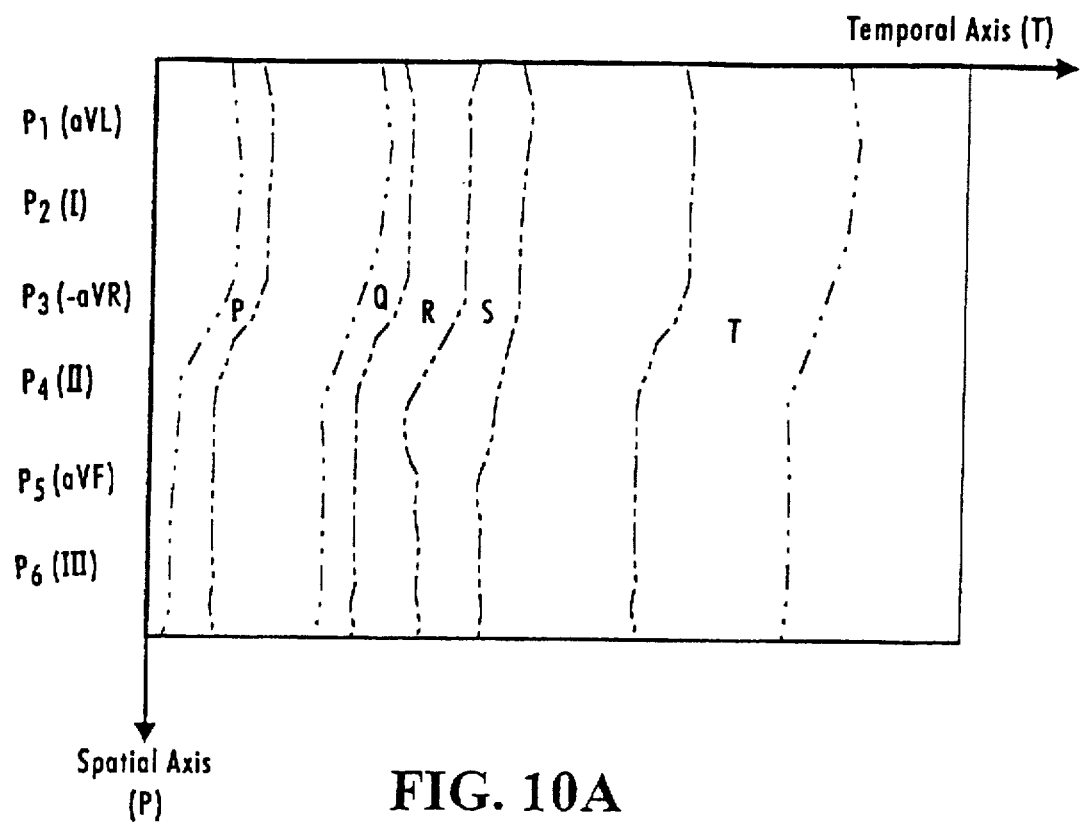
FIG. 10A is a schematic diagram of the top rectangular view of the 3-D representation of the frontal-plane cardiac signals.

Similar to the previous embodiment, the 3-D graph formed by the second preferred embodiment of the method of the invention can be displayed in a top rectangular view, as schematically illustrated in FIG. 10A. For each heartbeat of the patient, the top rectangular view shows a P-wave region, a QRS-complex wave, and a T-wave region. These regions are displayed in the same manner as the previous embodiment so that description thereof will not be repeated. If the patient has a heart disease, the corresponding variations in the P-wave, QRS-complex wave, and T-wave in each of the cardiac signals [I, II, III, $\alpha V_L$, $\alpha V_R$, $\alpha V_F$] can here be collectively observed by the physicians by viewing one single 3-D graph instead of six 2-D graphs obtained by the conventional EKG method.

Figure 10B:
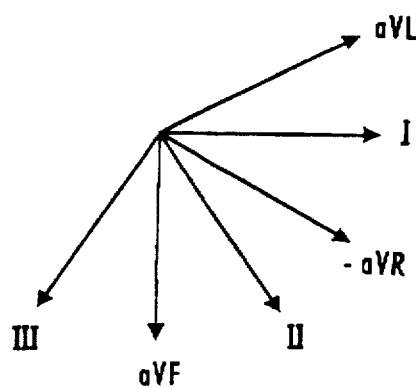
FIG. 10B is a schematic diagram of the top sectoral view showing the phase relationship among the frontal-plane cardiac signals displayed in the 3-D graph.

The physicians can also choose to display a top sectoral view as illustrated in FIG. 10B to see the phase relationship among the displayed cardiac signals.

In conclusion, the method of the invention allows the 12 cardiac signals [$V_1$, $V_2$, $V_3$, $V_4$, $V_5$, $V_6$] and [I, II, III, $\alpha V_L$, $\alpha V_R$, $\alpha V_F$] to be displayed in two 3-D graphs instead of twelve 2-D graphs as in the conventional EKG method for displaying the standard 12-lead EKG. This allows the physicians to observe the P-wave, QRS-complex wave, and T-wave in each of the six cardiac signals [$V_1$, $V_2$, $V_3$, $V_4$, $V_5$, $V_6$] collectively in one single 3-D graph, and those in each of the six cardiac signals [I, II, III, $\alpha V_L$, $\alpha V_R$, $\alpha V_F$] collectively in another 3-D graph. By viewing the 3-D graphs, the physicians can have an overall integral view over the plentiful number of cardiac signals. The physicians can thus make diagnoses more easily.

Before actual clinical application, the forms and features of the 3-D graphs corresponding to various heart diseases are prerecorded and built into a database for later comparison purpose in actual clinical applications. The method of the invention allows the physicians to observe the 3-D graph in various views for features indicative of specific heart diseases. The shape and color formation of the P-region, QRS-region, and T-region in the top rectangular view of the 3-D graph are particularly distinctive features indicative of specific heart diseases.

From the foregoing description, it is apparent that the invention provides an improved diagnostic tool which allows the physicians to make diagnoses of heart diseases more easily.

The invention has been described using exemplary preferred embodiments. However, it is to be understood that the scope of the invention is not limited to the disclosed embodiments. To the contrary, it is intended to cover various modifications and similar arrangements. The scope of the claims, therefore, should be accorded the broadest interpretation so as to encompass all such modifications and similar arrangements.

What is claimed is:

1. A 3-D EKG display method, comprising the steps of:
   (1) obtaining a plurality of cardiac signals from a patient;
   (2) defining a 3-D rectangular coordinate system having a temporal axis representing the time domain of the cardiac signals, a spatial axis representing the spatial positions from which the cardiac signals are obtained, and an amplitude axis representing the amplitudes of the cardiac signals;
   (3) defining an amplitude display scheme in which each quantization level of the amplitude of each of the cardiac signals is mapped to a predetermined visual display manner;
   (4) displaying a 3-D representation of the cardiac signals based on the 3-D rectangular coordinate system defined in said step (2) and the amplitude display scheme defined in said step (3); and
   (5) displaying a selected aspect of the 3-D representation of the cardiac signals in accordance with a user-selection.

2. The 3-D EKG display method of claim 1, wherein in said step (1) the cardiac signals are obtained from a number of electrodes attached to the precordial curve on the patient's chest.

3. The 3-D EKG display method of claim 1, wherein in said step (1) the cardiac signals are the standard six frontal-plane cardiac signals.

4. The 3-D EKG display method of claim 3, further comprising the steps of:
   inverting the phase angle of at least one of the six frontal-plane cardiac signals such that the phase angles thereof are spaced substantially at nearly equal intervals; and
   arranging the six frontal-plane cardiac signal on the spatial axis of the 3-D rectangular coordinate system in a sequential order of the phase angles thereof.

5. The 3-D EKG display method of claim 1, further comprising:
   a preprocessing step after said step (1) for eliminating noise and drift effect in the cardiac signals.

6. The 3-D EKG display method of claim 1, wherein in said step (3) the amplitude display scheme includes an amplitude-to-color mapping table which assigns each quantization level of amplitude to one specified color.

7. The 3-D EKG display method of claim 1, wherein in said step (3) the amplitude display scheme includes an amplitude-to-grayscale mapping table which assigns each quantization level of amplitude to one gray level in a grayscale.

8. The 3-D EKG display method of claim 1, wherein in said step (3) the amplitude display scheme displays equal quantization levels of amplitude by a number of contour lines.

9. The 3-D EKG display method of claim 1, further comprising the step of:
   obtaining the amplitude values of intermediate spatial points between the cardiac signals by interpolation.

10. The 3-D EKG display method of claim 1, further comprising the step of:
    displaying a top rectangular view of the 3-D graph which is a 2-D graph showing the amplitude distribution of the cardiac signals.

11. The 3-D EKG display method of claim 1, further comprising the step of:
    displaying a top sectoral view of the 3-D graph which shows the phase relationship among the cardiac signals.

12. The 3-D EKG display method of claim 1, further comprising the step of:
    displaying the 3-D graph in a perspective view in a specified aspect according to a user-selection.

13. The 3-D EKG display method of claim 12, wherein the perspective view of the 3-D graph is displayed in a static display manner which displays the 3-D representation of the cardiac signals extracted during a fixed period within each heartbeat of the patient.

14. The 3-D EKG display method of claim 12, wherein the perspective view of the 3-D graph is displayed in a dynamic display manner which refreshes the 3-D representation of the cardiac signals with each heartbeat of the patient.

15. The 3-D EKG display method of claim 1, further comprising the step of:

displaying a V-T plane sectional view of the 3-D graph to show the amplitude-time characteristic of one selected cardiac signal.

16. The 3-D EKG display method of claim 1, further comprising the step of:

displaying a P-T plane sectional view of the 3-D graph to show the amplitude distribution of all of the cardiac signals over the precordial curve on the patient's chest at a selected time.

17. An EKG display method for 3-D representation of the six horizontal-plane cardiac signals, comprising the steps of:

(1) obtaining a set of cardiac signals from a number of electrodes attached on the precordial curve on the chest of a patient;

(2) defining a 3-D rectangular coordinate system having a temporal axis representing the time domain of the horizontal-plane cardiac signals, a spatial axis representing the spatial positions from which the horizontal-plane cardiac signals are obtained, and an amplitude axis representing the amplitudes of the horizontal-plane cardiac signals;

(3) defining an amplitude display scheme in which each quantization level of the amplitude of each of the cardiac signals is mapped to a predetermined visual display manner;

(4) displaying a 3-D representation of the cardiac signals based on the 3-D rectangular coordinate system defined in said step (2) and the amplitude display scheme defined in said step (3); and (5) displaying a selected aspect of the 3-D representation of the cardiac signals in accordance with a user-selection.

18. An EKG display method for 3-D representation of the six frontal-plane cardiac signals, comprising the steps of:

(1) obtaining the six frontal-plane cardiac signals from a patient;

(2) defining a 3-D rectangular coordinate system having a temporal axis representing the time domain of the frontal-plane cardiac signals, a spatial axis representing the spatial positions from which the frontal-plane cardiac signals are obtained, and an amplitude axis representing the amplitudes of the frontal-plane cardiac signals;

(3) defining an amplitude display scheme in which each quantization level of the amplitude of each of the cardiac signals is mapped to a predetermined visual display manner;

(4) displaying a 3-D representation of the cardiac signals based on the 3-D rectangular coordinate system defined in said step (2) and the amplitude display scheme defined in said step (3); and (5) displaying a selected aspect of the 3-D representation of the cardiac signals in accordance with a user-selection.

19. The EKG display method of claim 18, further comprising the steps of:

inverting the phase angle of at least one of the six frontal-plane cardiac signals such that the phase angles thereof are spaced substantially at nearly equal intervals; and arranging the six frontal-plane cardiac signal on the spatial axis of the 3-D rectangular coordinate system in a sequential order of the phase angles thereof.

* * * * *

UNITED STATES PATENT AND TRADEMARK OFFICE
CERTIFICATE OF CORRECTION

PATENT NO. : 5,782,773
DATED : July 21, 1998
INVENTOR(S) : Cheng-Deng KUO et al

It is certified that error appears in the above-identified patent and that said Letters Patent is hereby corrected as shown below:

On the title page item [73], under Assignee, replace "Chih-Wei Chen" with --Hui-Hua Chiang---

Signed and Sealed this

Fourteenth Day of September, 1999

Attest:

Q. TODD DICKINSON

*Attesting Officer*     *Acting Commissioner of Patents and Trademarks*